(12) United States Patent
Hanazawa et al.

(10) Patent No.: US 7,566,739 B2
(45) Date of Patent: Jul. 28, 2009

(54) SUBSTITUTED N-SULFONYLAMINOPHENYLETHYL-2-PHENOXYACETAMIDE COMPOUNDS AS VR1 RECEPTOR ANTAGONISTS

(75) Inventors: Takeshi Hanazawa, Aichi-ken (JP); Misato Hirano, Aichi-ken (JP); Tadashi Inoue, Aichi-ken (JP); Satoshi Nagayama, Aichi-ken (JP); Kazunari Nakao, Aichi-ken (JP); Yuji Shishido, Aichi-ken (JP); Hirotaka Tanaka, Aichi-ken (JP)

(73) Assignee: Pfizer Inc., New York, NY (US)

( * ) Notice: Subject to any disclaimer, the term of this patent is extended or adjusted under 35 U.S.C. 154(b) by 41 days.

(21) Appl. No.: 11/372,706

(22) Filed: Mar. 10, 2006

(65) Prior Publication Data

US 2006/0205980 A1    Sep. 14, 2006

Related U.S. Application Data

(60) Provisional application No. 60/660,978, filed on Mar. 10, 2005.

(51) Int. Cl.
*A61K 31/18*    (2006.01)
*C07C 311/09*    (2006.01)
*C07C 311/08*    (2006.01)

(52) U.S. Cl. .......................... 514/605; 564/99
(58) Field of Classification Search .................. 564/99; 514/605
See application file for complete search history.

(56) References Cited

U.S. PATENT DOCUMENTS

| 7,214,824 B2 * | 5/2007 | Inoue et al. ............... 564/94 |
| 2002/0091116 A1 | 7/2002 | Zhu et al. |
| 2004/0116399 A1 | 6/2004 | Zhu et al. |
| 2005/0085449 A1 | 4/2005 | Dalton et al. |

FOREIGN PATENT DOCUMENTS

| EP | 0241043 | 10/1987 |
| WO | WO9631475 | 10/1996 |
| WO | WO0119788 | 3/2001 |
| WO | WO0119798 | 3/2001 |
| WO | WO0164642 | 9/2001 |
| WO | WO0216318 | 2/2002 |
| WO | WO0216319 | 2/2002 |
| WO | WO03031394 | 4/2003 |
| WO | WO03097047 | 11/2003 |
| WO | WO2004035533 | 4/2004 |
| WO | WO 2005/003084 A1 | 1/2005 |
| WO | WO2005040093 | 5/2005 |

OTHER PUBLICATIONS

C. Deal, et al., "Treatment of Arthritis with Topical Capsaicin:Double-Blind Trial", Clin Ther, 1991, pp. 383-395, vol. 13, No. 3.
J. Fernihough, et al., "Regulation of Calcitonin Gene-related Peptide and TRPV1 in a Rat Model of Osteoarthritis", Neuroscience Letters, Nov. 2005, pp. 75-80, vol. 388, No. 2.
P. Honore, et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats", J Pharmacol Exp Ther, 2005, pp. 410-421, vol. 314 No. 1.
R. Planells-Cases, et al., Functional Aspects and Mechanisms of TRPV1 Involvement in Neurogenic Inflammation that Leads to Thermal Hyperalgesia, Eur J Physiol, 2005, pp. 151-159, vol. 451.

* cited by examiner

*Primary Examiner*—Peter G O'Sullivan
(74) *Attorney, Agent, or Firm*—Gregg C. Benson; A. Dean Olson

(57) ABSTRACT

This invention provides compounds of the formula (I) useful for the treatment of disease conditions caused by over activation of Vr1 receptors such as pain or the like in mammals as well as compositions comprising them.

12 Claims, No Drawings

SUBSTITUTED N-SULFONYLAMINOPHENYLETHYL-2-PHENOXYACETAMIDE COMPOUNDS AS VR1 RECEPTOR ANTAGONISTS

This application is a United States utility non-provisional application, which claims the benefit of priority to U.S. Provisional Application No. 60/660,978, filed Mar. 10, 2005.

TECHNICAL FIELD

This invention relates to novel substituted N-sulfonylaminophenylethyl-2-phenoxyacetamide compounds. These compounds are useful as antagonists of the VR1 (Type I Vanilloid) receptor, and are thus useful for the treatment of pain, neuralgia, neuropathies, nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds.

BACKGROUND ART

The Vanilloid receptor 1 (VR1) is a ligand gated non-selective cation channel. It is believed to be a member of the transient receptor potential super family. VR1 is recognized as a polymodal nociceptor that integrates multiple pain stimuli, e.g., noxious heat, protons, and vanilloids (European Journal of Physiology 451:151-159, 2005). A major distribution of VR1 is in the sensory (Aδ- and C—) fibers, which are bipolar neurons having somata in sensory ganglia. The peripheral fibers of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, have suggested that VR1 positive nerves are thought to participate in a variety of physiological responses, including nociception (Clinical Therapeutics. 13(3): 338-395, 1991, Journal of Pharmacology and Experimental Therapeutics 314:410-421, 2005, and Neuroscience Letter 388: 75-80, 2005). Based on both the tissue distribution and the roles of VR1, VR1 antagonists would have good therapeutic potentials.

International Patent Application Number WO-A-2005003084 discusses 4-(methylsulfonylamino) phenyl analogues which are stated to have activity as VR1 antagonists.

It would be desirable if there were provided a novel VR1 selective antagonist with improved binding activity with the VR1 receptor by systemic administration and with a good half-life. Other potential advantages include less toxicity, good absorption, good solubility, low protein binding affinity, less drug-drug interaction, a reduced inhibitory activity at HERG channel, reduced QT prolongation and good metabolic stability.

BRIEF DISCLOSURE OF THE INVENTION

It has now been found that substituted N-sulfonylaminobenzyl-2-phenoxyacetamide compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at HERG channel, reduced QT prolongation and good metabolic stability.

The present invention provides a compound of the following formula (I):

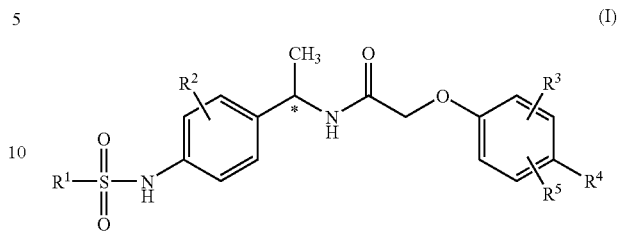

wherein $R^1$ represents $(C_1\text{-}C_6)$alkyl;
$R^2$ represents hydrogen, halogen, hydroxy, $(C_1\text{-}C_6)$alkyl, $(C_1\text{-}C_6)$alkoxy, hydroxy$(C_1\text{-}C_6)$alkyl, $(C_1\text{-}C_6)$ alkoxy-$(C_1\text{-}C_6)$alkyl or halo$(C_1\text{-}C_6)$alkyl;
$R^3$ represents a halogen atom, $(C_1\text{-}C_6)$alkyl, $(C_1\text{-}C_6)$alkoxy, hydroxy$(C_1\text{-}C_6)$alkoxy, $(C_1\text{-}C_6)$alkoxy-$(C_1\text{-}C_6)$ alkyl, $(C_1\text{-}C_6)$alkoxy-$(C_1\text{-}C_6)$alkoxy, halo$(C_1\text{-}C_6)$alkyl, $(C_1\text{-}C_6)$alkylthio, $(C_1\text{-}C_6)$alkylsulfinyl, $(C_1\text{-}C_6)$ alkylsulfonyl, $[(C_1\text{-}C_6)\text{alkyl}]\text{NH}$—, or $[(C_1\text{-}C_6)\text{alkyl}]_2\text{N}$—;
$R^4$ represents a halogen atom, $(C_1\text{-}C_6)$alkyl, halo$(C_1\text{-}C_6)$alkyl, $(C_1\text{-}C_6)$alkoxy, hydroxy$(C_1\text{-}C_6)$alkoxy, $(C_1\text{-}C_6)$alkoxy-$(C_1\text{-}C_6)$alkyl, $(C_1\text{-}C_6)$alkoxy-$(C_1\text{-}C_6)$alkoxy, $[(C_1\text{-}C_6)\text{alkyl}]\text{NH}$—, or $[(C_1\text{-}C_6)\text{alkyl}]_2\text{N}$—;
$R^5$ represents a halogen atom, $(C_1\text{-}C_6)$alkyl, $(C_1\text{-}C_6)$alkoxy, hydroxy$(C_1\text{-}C_6)$alkoxy, $(C_1\text{-}C_6)$alkoxy-$(C_1\text{-}C_6)$ alkyl, $(C_1\text{-}C_6)$alkoxy-$(C_1\text{-}C_6)$alkoxy, halo$(C_1\text{-}C_6)$alkyl, $(C_1\text{-}C_6)$ alkylthio, $(C_1\text{-}C_6)$alkylsulfinyl, $(C_1\text{-}C_6)$ alkylsulfonyl, $[(C_1\text{-}C_6)\text{alkyl}]\text{NH}$—, $[(C_1\text{-}C_6)\text{alkyl}]_2\text{N}$—, $H_2\text{N}$—$(C_1\text{-}C_6)$ alkoxy, $(C_1\text{-}C_6)$alkyl-NH—$(C_1\text{-}C_6)$alkoxy, $[(C_1\text{-}C_6)$alkyl$]_2$ N$(C_1\text{-}C_6)$alkoxy, $H_2\text{N}$—$(C_1\text{-}C_6)$alkoxy-$(C_1\text{-}C_6)$ alkyl, $(C_1\text{-}C_6)$alkyl-NH—$(C_1\text{-}C_6)$alkoxy-$(C_1\text{-}C_6)$alkyl, or $[(C_1\text{-}C_6)\text{alkyl}]_2\text{N}(C_1\text{-}C_6)\text{alkoxy-}(C_1\text{-}C_6)\text{alkyl}$; and
* indicates a chiral centre;
or a pharmaceutically acceptable salt or solvate thereof.

DETAILED DESCRIPTION OF THE INVENTION

As used herein, the term "halogen" means fluoro, chloro, bromo and iodo, preferably fluoro or chloro.

As used herein, the term "$(C_1\text{-}C_6)$alkyl" means straight or branched chain saturated radicals having from one to six carbon atoms, including, but not limited to methyl, ethyl, n-propyl, iso-propyl, n-butyl, iso-butyl, secondary-butyl, tertiary-butyl. Preferable alkyl groups are methyl, ethyl, n-propyl, n-butyl, tertiary-butyl.

As used herein, the term "hydroxy$(C_1\text{-}C_6)$alkyl" means a $(C_1\text{-}C_6)$alkyl radical as defined above which is substituted by hydroxy group including, but not limited to, hydroxymethyl, hydroxyethyl, hydroxy n-propyl, hydroxyisopropyl, hydroxy n-butyl, hydroxy iso-butyl, hydroxy secondary-butyl, hydroxy tertiary-butyl. Preferable hydroxyalkyl groups are hydroxymethyl, hydroxyethyl, hydroxy n-propyl, hydroxy n-butyl.

As used herein, the term "$(C_1\text{-}C_6)$alkoxy" means $(C_1\text{-}C_6)$ alkyl-O—, including, but not limited to methoxy, ethoxy, n-propoxy, iso-propoxy, n-butoxy, iso-butoxy, secondary-butoxy, tertiary-butoxy. Preferable alkoxy groups are methoxy, ethoxy, n-propoxy, n-butoxy, tertiary-butoxy.

As used herein, the term "hydroxy$(C_1\text{-}C_6)$alkoxy" means a $(C_1\text{-}C_6)$alkoxy radical as defined above which is substituted by hydroxy group including, but not limited to, hydroxymethoxy, hydroxyethoxy, hydroxy n-propoxy, hydroxyisopropoxy, hydroxy n-butoxy, hydroxy iso-butoxy, hydroxy secondary-butoxy, hydroxy tertiary-butoxy. Preferable hydroxyalkoxy groups are hydroxymethoxy, hydroxyethoxy, hydroxy n-propoxy, hydroxy n-butoxy.

As used herein, the term "$(C_1-C_6)$alkylthio" means $(C_1-C_6)$alkyl-S— wherein $(C_1-C_6)$alkyl is defined above, including, but not limited to methylthio, ethylthio, r-propylthio, iso-propylthio, n-butylthio, iso-butylthio, secondary-butylthio, tertiary-butylthio. Preferable alkylthio groups are methylthio, ethylthio, n-propylthio, n-butylthio.

As used herein, the term "$(C_1-C_6)$alkylsulfinyl" means $(C_1-C_6)$alkyl-SO— wherein $(C_1-C_6)$alkyl is defined above, including, but not limited to methylsulfinyl, ethylsulfinyl, n-propylsulfinyl, iso-propylsulfinyl, n-butylsulfinyl, iso-butylsulfinyl, secondary-butylsulfinyl, tertiary-butylsulfinyl. Preferable alkylsulfinyl groups are methylsulfinyl, ethylsulfinyl, n-propylsulfinyl, n-butylsufinyl.

As used herein, the term "$(C_1-C_6)$alkylsulfonyl" means $(C_1-C_6)$alkyl-$SO_2$— wherein $(C_1-C_6)$alkyl is defined above, including, but not limited to methylsulfonyl, ethylsulfonyl, n-propylsulfonyl, iso-propylsulfonyl, n-butylsulfonyl, iso-butylsulfonyl, secondary-butylsulfonyl, tertiary-butylsulfonyl. Preferable alkylsulfonyl groups are methylsulfonyl, ethylsulfonyl, n-propylsulfonyl, n-butylsulfonyl.

As used herein, the term ""$[(C_1-C_6)$alkyl]NH—" means $(C_1-C_6)$alkyl-NH— wherein $(C_1-C_6)$alkyl is defined above, including, but not limited to methylamino, ethylamino, n-propylamino, iso-propylamino, n-butylamino, iso-butylamino, secondary-butylamino, tertiary-butylamino. Preferable alkylamino groups are methylamino, ethylamino, n-propylamino, n-butylamino.

As used herein, the term "$[(C_1-C_6)$alkyl$]_2$N—" means di$((C_1-C_6)$alkyl)-N— wherein $(C_1-C_6)$alkyl is defined above, including, but not limited to dimethylamino, diethylamino, methylethylamino, di n-propylamino, methyl n-propylamino, ethyl n-propylamino di iso-propylamino, di n-butylamino, methyl n-butylamino di iso-butylamino, di secondary-butylamino, di tertiary-butylamino. Preferable dialkylamino groups are dimethylamino, diethylamino, di n-propylamino, di n-butylamino.

As used herein the term "halo$(C_1-C_6)$alkyl", means a $(C_1-C_6)$alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups. Preferable haloalkyl groups are fluoromethyl, difluoromethyl, trifluoromethyl, 2-fluoroethyl, 2,2-difluoroethyl, 2,2,2-trifluoroethyl, Where the compounds of formula (I) contain hydroxy groups, they may form esters. Examples of such esters include esters with esters with a carboxy group. The ester residue may be an ordinary protecting group or a protecting group which can be cleaved in vivo by a biological method such as hydrolysis.

Preferably $R^1$ represents methyl, and $R^2$ $R^3$, $R^4$ and $R^5$ are each as defined above.

Preferably $R^2$ represents hydrogen, fluoro, chloro, hydroxy, hydroxymethylene or methoxy, $R^1$ is either as defined above in its broadest definition or is methyl, and $R^3$, $R^4$ and $R^5$ are each as defined above.

Preferably $R^3$ represents halogen or $(C_1-C_3)$alkoxy, most preferably fluoro, $R^1$ and $R^2$ are as defined above either in the broadest or the preferred definitions, and $R^4$ and $R^5$ are each as defined above.

Preferably $R^4$ represents $(C_1-C_6)$alkyl, or halo$(C_1-C_6)$alkyl, most preferably tert-butyl or 2,2,2-trifluoro-1,1-dimethylethyl, $R^1$, $R^2$ and $R^3$ are each as defined above either in the broadest or the preferred definitions, and $R^5$ is as defined above.

Preferably $R^5$ represents halogen or $(C_1-C_3)$alkoxy, most preferably fluoro, and $R^1$, $R^2$, $R^3$ and $R^4$ are each as defined above, either in the broadest or in the preferred definitions.

Preferred individual compounds of this invention are selected from 2-(4-tert-butyl-3,5-difluorophenoxy)-N-(1-{3-methyl-4-[(methylsulfonyl)amino]phenyl}ethyl)acetamide;

2-(4-tert-butyl-3,5-difluorophenoxy)-N-(1-{3-fluoro-4-[(methylsulfonyl)amino]phenyl}ethyl)acetamide;

2-(4-tert-butyl-3,5-difluorophenoxy)-N-(1-{4-[(methylsulfonyl)amino]phenyl}ethyl)acetamide;

2-(4-tert-butyl-3,5-difluorophenoxy)-N-(1-{3-hydroxymethyl-4-[(methylsulfonyl)amino]phenyl}ethyl)acetamide; and 2-(4-(2,2,2-trifluoro-1,1-dimethylethyl)-3,5-difluorophenoxy)-N-(1-{3-methyl-4-[(methylsulfonyl)amino]phenyl}ethyl)acetamide;

or a pharmaceutically acceptable salt or solvate thereof.

Most preferably the compounds of formula (I) have (R) stereochemistry at the position marked *.

Further preferred compounds of the invention include those in which each variable in Formula (I) is selected from the preferred groups for each variable.

The compounds of the present invention are antagonists of the VR1 receptor and are thus useful in therapeutics, particularly for the treatment of acute cerebral ischemia, pain, chronic pain, neuropathic pain, inflammatory pain, post herpetic neuralgia, neuropathies, neuralgia, -diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence, micturition disorder, renal colic and cystitis, inflammation, such as burns, rheumatoid arthritis and osteoarthritis, neurodegenerative disease, such as stroke, post stroke pain and multiple sclerosis, pulmonary disease, such as asthma, cough, chronic obstructive pulmonary disease (COPD) and broncho constriction, gastrointestinal, such as gastroesophageal reflux disease (GERD), dysphagia, ulcer, irritable bowel syndrome (IBS), inflammatory bowel disease (IBD), colitis and Crohn's disease, ischemia, such as cerebrovascular ischemia, emesis, such as cancer chemotherapy-induced emesis, and obesity, or the like in mammals, especially humans.

The compounds of formula (I), being VR1 antagonists, are potentially useful in the treatment of a range of disorders. The treatment of pain, particularly neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries-resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posuraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating. Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353,1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The present invention provides a pharmaceutical composition including a compound of formula (I), or a pharmaceutically acceptable salt or solvate thereof, together with a pharmaceutically acceptable excipient. The composition is preferably useful for the treatment of the-disease conditions defined above.

The present invention further provides a compound of formula (I), or a pharmaceutically acceptable salt or solvate thereof, for use as a medicament.

Further, the present invention provides a method for the treatment of the disease conditions defined above in a mammal, preferably a human, which includes administering to said mammal a therapeutically effective amount of a compound of formula (I), or a pharmaceutically acceptable salt or solvate thereof.

Yet further, the present invention provides the use of a compound of formula (I), or a pharmaceutically acceptable salt or solvate thereof, in the manufacture of a medicament for the treatment of the disease conditions defined above.

Yet further, the present invention provides a combination of a compound of the formula (I), or a pharmaceutically acceptable salt or solvate thereof, and another pharmacologically active agent.

General Synthesis

The compounds of the present invention may be prepared by a variety of processes well known for the preparation of compounds of this type, for example as shown in the following reaction Scheme. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999);

The following reaction scheme illustrates the preparation of compounds of formula (I).

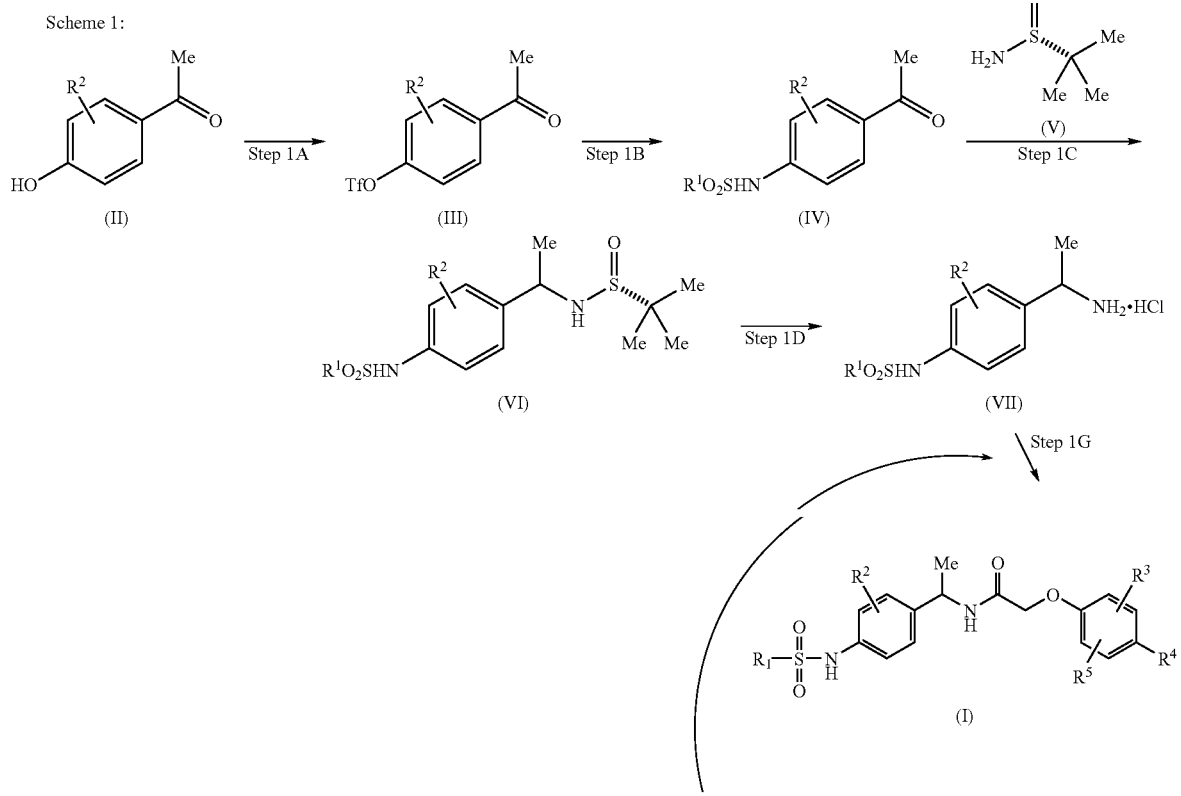

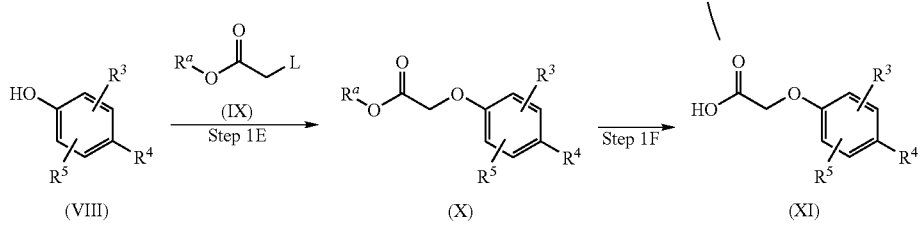

wherein L is a suitable leaving group such as a halogen, and is preferably chloro, bromo or iodo;
Me is methyl; and
Tf is triflate.

Step 1A

In this step, a compound of formula (III) can be prepared by reaction of a compound of formula (II) with a triflate source such as triflic anhydrate under basic conditions in an inert solvent.

A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine.

Examples of suitable solvents include: tetrahydrofuran; 1,4-dioxane; N,N-dimethylformamide; acetonitrile; alcohols, such as methanol or ethanol; halogenated hydrocarbons, such as dichloromethane, 1,2-dichloroethane, chloroform or carbon tetrachloride; and acetic acid.

Reaction temperatures are generally in the range of from −78° C. to 200° C., preferably in the range of from 0° C. to room temperature. Reaction times are, in general, from 1 minute to a day, preferably from 1 hour to 20 hours.

Step 1B

In this step, a compound of formula (IV) can be prepared by a coupling reaction of a compound of formula (III) with alkyl sulfonamide under basic conditions in the presence of a catalyst and Xantphos in an inert solvent, as described in Buchwald, S. L. Journal of American chemical society, 2002, 124, 6043-6048.

Examples of suitable catalysts include tris(dibenzylidenacetone)dipalladium (0), and palladium reagents, such as palladium acetate and palladium dibenzylacetone.

A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, 2,6-lutidine, pyridine or dimethylaminopyridine.

Examples of suitable solvents include: tetrahydrofuran; 1,4-dioxane; N,N-dimethylformamide; acetonitrile; alcohols, such as methanol or ethanol; halogenated hydrocarbons, such as dichloromethane, 1,2-dichloroethane, chloroform or carbon tetrachloride; and acetic acid.

Reaction temperatures are generally in the range of from 0° C. to 200° C., preferably in the range of from 100° C. to 140° C. Reaction times are, in general, from 1 minute to a day, preferably from 5 minutes to 1 hour.

Step 1C

In this step, a compound of formula (VI) can be prepared by dehydration and reduction of a compound of formula (IV) with a sulfimamide of formula (V) in the presence of a catalyst and reduction agent in a reaction-inert solvent.

The dehydration reaction is conducted in the presence of a dehydrating agent. Examples of suitable dehydrating agents include: hydrogen halide, such as hydrogen chloride and hydrogen bromide; sulfonic acids, such as p-toluenesulfonic acid and benzenesulfonic acid; sulfonylchloride, such as methanesulfonylchloride and p-toluenesulfonylchloride; (methoxycarbonylsulfamoyl)triethylammonium hydroxide; p-toluenesulfonylisocyanate; and titanium(IV)ethoxide.

Reaction temperatures are generally in the range of from 0° C. to 200° C., preferably in the range of from 50° C. to 100° C. Reaction times are, in general, from 1 minute to 48 hours, preferably from 12 hours to 24 hours.

The reduction may be carried out in the presence of a suitable reducing agent in an inert solvent or without solvent. A preferred reducing agent is selected from, for example, but not limited to, NaBH$_4$, LiAlH$_4$, LiBH$_4$, Fe, Sn or Zn.

Reaction temperatures are generally in the range of from −78° C. to room temprature, preferably in the range of from −70° C. to 0° C. Reaction times are, in general, from 1 minute to a day, preferably from 3 hours to 6 hours.

Examples of suitable solvents include: tetrahydrofuran; 1,4-dioxane; N,N-dimethylformamide; acetonitrile; alcohols, such as methanol or ethanol; halogenated hydrocarbons, such as dichloromethane, 1,2-dichloroethane, chloroform or carbon tetrachloride; and acetic acid.

Step 1D

In this step, a compound of formula (VII) can be prepared by deprotection and salt formation of a compound of formula (VI) under acidic conditions in an inert solvent using the method described by D. Cogan et. al. in the Journal of American Chemical Society, 1999, 121, 268-269.

Reaction temperatures are generally in the range of from 0° C. to 200° C., preferably room temperature. Reaction times are, in general, from 1 minute to 24 hours, preferably from 5 minutes to 1 hour.

Examples of suitable solvents include: tetrahydrofuran; 1,4-dioxane; N,N-dimethylformamide; acetonitrile; alcohols, such as methanol or ethanol; halogenated hydrocarbons, such as dichloromethane, 1,2-dichloroethane, chloroform or carbon tetrachloride; and acetic acid.

Step 1E

In this step, a compound of formula (X) can be prepared by the substitution reaction of a compound of formula (VII) with a compound of formula (IX) in the presence of a base in an inert solvent. Examples of suitable solvents include: tetrahydrofuran, N,N-dimethylformamide, dimethylsulfoxide, diethylether, toluene, ethylene glycol dimethylether generally or 1,4-dioxane. Preferred solvents are tetrahydrofuran, N,N-dimethylformamide, dimethylsulfoxide, and 1,4-dioxane. Examples of suitable bases include: alkyl lithiums, such as n-butyllithium, sec-butyllithium or tert-butyllithium; aryllithiums, such as phenyllithium or lithium naphthalide; metal amide such as sodium amide or lithium diisopropylamide; alkali metal hydride, such as potassium hydride or sodium hydride; and alkali metal carbonate, such as potassium carbonate or sodium carbonate. Preferred bases are n-butyllithium, tert-butyllithium, potassium hydride and potassium carbonate. This reaction can be carried out at a temperature in the range of from −50° C. to 200° C., usually from 0° C. to 80° C. for from 5 minutes to 72 hours, usually 30 minutes to 24 hours.

Step 1F

In this Step, an acid compound of formula (XI) can be prepared by hydrolysis of the ester compound of formula (X) in a suitable solvent.

The hydrolysis can be carried out by conventional procedures. In a typical procedure, the hydrolysis is carried out under basic conditions, e.g. in the presence of sodium hydroxide, potassium hydroxide or lithium hydroxide. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). Preferred solvents are methanol, ethanol, propanol, tetrahydrofuran (THF), dimethoxyethane (DME), 1,4-dioxane, N,N-dimethylformamide (DMF), and dimethyl sulfoxide (DMSO). This reaction can be carried out at a temperature in the range of from −20° C. to 100° C., usually from 20° C. to 65° C. for from 30 minutes to 24 hours, usually 60 minutes to 10 hours.

The hydrolysis can also be carried out under acidic conditions, e.g. in the presence of hydrogen halides, such as hydrogen chloride and hydrogen bromide; sulfonic acids, such as p-toluenesulfonic acid and benzenesulfonic acid; pyridinium p-toluenesulfonate; or carboxylic acids, such as acetic acid and trifluoroacetic acid. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,N-dimethylformamide (DMF) and hexamethylphosphorictriamide; and sulfoxides such as dimethyl sulfoxide (DMSO). Preferred solvents are methanol, ethanol, propanol, tetrahydrofuran (THF), dimethoxyethane (DME), 1,4-dioxane, N,N-dimethylformamide (DMF), and dimethyl sulfoxide (DMSO). This reaction can be carried out at a temperature in the range of from −20° C. to 100° C., usually from 20° C. to 65° C. for from 30 minutes to 24 hours, usually 60 minutes to 10 hours.

Step 1G

In this Step, an amide compound of formula (I) can be prepared by the coupling reaction of an amine compound of formula (VII) with the acid compound of formula (XI) in the presence or absence of a coupling reagent in an inert solvent. This reaction can be carried out through activated carboxylic derivatives.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; sulfolane; DMSO; N-methylpyrrolidone (NMP); 2-butanone; acetonitrile; halogenated hydrocarbons, such as dichloromethane, dichloroethane, chloroform; and ethers, such as tetrahydrofuran and dioxane.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Suitable coupling reagents are those typically used in peptide synthesis including, for example, diimides (e.g., dicyclohexylcarbodiimide (DCC) and 1-ethyl-3-(3'dimethylaminopropyl)-carbodiimide hydrochloride (EDC)), 2-ethoxy-N-ethoxycarbonyl-1,2-dihydroquinoline, 2-bromo-1-ethylpyridinium tetrafluoroborate (BEP), 2-chloro-1,3-dimethylimidazolinium chloride (CDI), benzotriazol-1-yloxy-tris(dimethylamino)phosphonium hexafluorophosphate (BOP), diethyl azodicarboxylate-triphenylphosphine, diethylcyanophosphate, diethylphosphorylazide, 2-chloro-1-methylpyridinium iodide, N, N'-carbonyidiimidazole, benzotriazole-1-yl diethyl phosphate, ethyl chloroformate or isobutyl chloroformate.

The reaction can be carried out in the presence of a base such as, 1-hydroxybenzotriazole (HOBt), N,N-diisopropylethylamine, N-methylmorpholine and triethylamine. The amide compound of formula (I) can be formed via an acylhalide, which can be obtained by reaction with halogenating agents such as oxalylchloride, phosphorus oxychloride and thionyl chloride. The resulting acylhalide can be converted to the corresponding amide compound by treating with an amine compound of formula (VII) under similar conditions as described in this Step.

The starting materials in the aforementioned general syntheses are commercially available or may be obtained by conventional methods known to those skilled in the art. However, additional information for synthesizing certain phenols of formula (VIII) is described in Scheme 2 below.

Scheme 2:

When $R^4$ is tert-butyl or 2,2,2-trifluoro-1,1-dimethylethyl, compounds of formula (VIII) may be prepared as illustrated in Scheme 2.

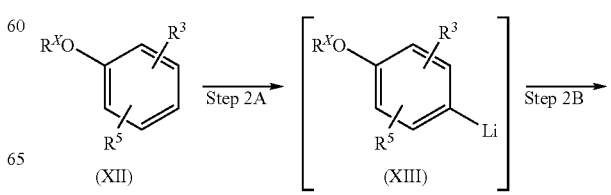

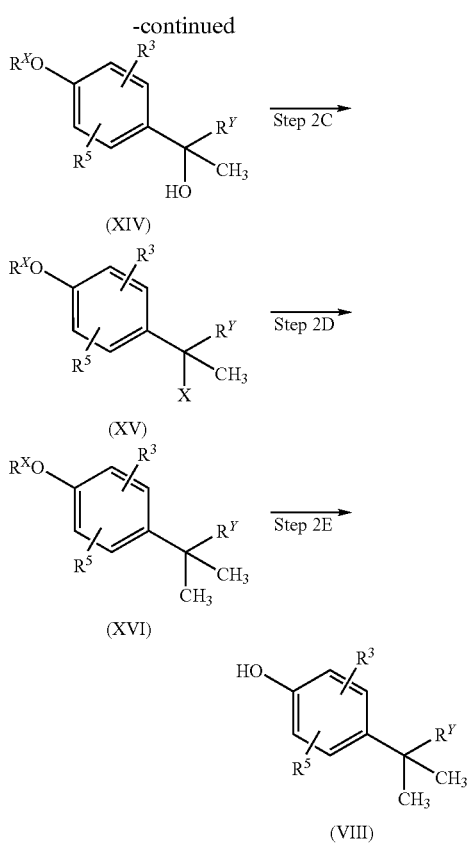

wherein R^x is a suitable protecting group such as $(C_1-C_6)$ alkyl, benzyl, benzoyl or $(C_1-C_6)$alkylsilyl; and is preferably methyl;
R^y is methyl or trifluoromethyl; and
X is halogen.

Step 2A

In this Step, an organolithium compound of formula (XIII) can be prepared by a directed metalation reaction of a compound of formula (XII) with an alkyllithum. This reaction may be carried out in the presence of an organometallic reagent or metal. Examples of suitable organometallic reagents include; alkyllithiums such as n-butyllithium, sec-butyllithium and tert-butyllithium; and aryllithiums, such as phenyllithium and lithium naphthalide. Preferred reaction inert solvents include, for example, hydrocarbons, such as hexane; ethers, such as diethyl ether, diisopropyl ether, dimethoxyethane (DME), tetrahydrofuran (THF) and 1,4-dioxane; or mixtures thereof. Reaction temperatures are generally in the range of from −100° C. to 50° C., preferably in the range of from −100° C. to room temperature. Reaction times are, generally, from 1 minute to a day, preferably from 1 hour to 10 hours.

Step 2B

In this step, a compound of formula (XIV) can be prepared by the nucleophilic addition of a compound of formula (XIII) with a ketone. Examples of suitable ketone reagents include acetone and 1,1,1-trifluoroacetone. Preferred inert solvents include, for example, hydrocarbons, such as hexane; ethers, such as diethyl ether, diisopropyl ether, dimethoxyethane (DME), tetrahydrofuran (THF) and dioxane; or mixtures thereof. Reaction temperatures are generally in the range of from −100° C. to 50° C., preferably in the range of from −100° C. to room temperature. Reaction times are, in general, from 1 minute to a day, preferably from 1 hour to 10 hours.

Step 2C

In this step, a compound of formula (XV) can be prepared by the halogenation reaction of a compound of formula (XIV) with a halogenating agent. The halogenation may be carried out in the present of a suitable halogenating agent in an inert solvent or without solvent. Preferred inert solvents include, for example, hydrocarbons, such as benzene, toluene, xylene; halogenated hydrocarbons, such as dichloromethane, 1,2-dichloroethane, chloroform or carbon tetrachloride; or mixtures thereof. A preferred halogenating agent is selected from, but is not limited to, the following examples thionyl chloride, oxalyl chloride, phosphorus oxychloride, titanium chloride, phosphorus pentachloride, and is optionally combined with catalytic pyridine. Preferably the halogenating agent is the combination of thionyl chloride and catalytic pyridine. Reaction temperatures are generally in the range of from −100° C. to 200° C., preferably in the range of from −40° C. to 100° C. Reaction times are, generally, from 1 minute to a day, preferably from 1 hour to 10 hours.

Step 2D

In this Step, a compound of formula (XVI) can be prepared by a substitution reaction of a compound of formula (XV) with an alkylating agent. The alkylation may be carried out in the presence of a suitable alkylating agent in an inert solvent. Preferred inert solvents include, for example, halogenated hydrocarbons, such as dichloromethane, 1,2-dichloroethane, chloroform or carbon tetrachloride; ethers, such as diethyl ether, diisopropyl ether, DME, THF)and 1,4-dioxane; hydrocarbons, such as n-hexane, cyclohexane, benzene, toluene; or mixtures thereof. A preferred alkylating agent is selected from, but is not limited to, the following examples trialkylmetal such as trimethylaluminum, triethylaluminum; alkylmagnesium halide, such as methylmagnesium bromide, in the presence of additive compound such as lithium bromide; dialkylzinc halide such as dimethylzinc dichloride prepared from dimethylzinc and titanium chloride; and is preferably trimethylaluminum. Reaction temperatures are generally in the range of from −100° C. to 200° C., preferably in the range of from −40° C. to 100C. Reaction times are, generally, from 1 minute to a day, preferably from 1 hour to 10 hours.

Step 2E

In this Step, a compound of formula (VIII) can be prepared by deprotection of a compound of formula (XVI) with a deprotection agent in an inert solvent. Examples of suitable deprotection agents include: boron halide such as boron tribromide, boron trichloride; and hydrogen halide, such as hydrogen bromide. Preferred inert solvents include, for example, halogenated hydrocarbons such as dichloromethane, 1,2-dichloroethane, chloroform or carbon tetrachloride; and acetic acid. Reaction temperatures are generally in the range of from −100° C. to 200° C., preferably in the range of from −80° C. to 80° C. Reaction times are, generally, from 1 minute to a day, preferably from 1 hour to 10 hours.

The compounds of formula (I), and the intermediates of the above-mentioned preparation methods can be isolated and purified by conventional procedures, such as recrystallization or chromatographic purification.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Method for Assessing Biological Activities:

Human VR1 Antagonist Assay

VR1 antagonistic activity can be determined by the $Ca^{2+}$ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp 816-824, 1997. Alternatively VR1 receptors highly expressing human keratinocytes are also known and published in the journal article (Biochemical and Biophysical Research Communications, 291, pp 124-129, 2002). In this article, human keratinocytes demonstrated VR1 mediated intracellular $Ca^{2+}$ increase by addition of capsaicin. Furthermore, the method to upregulate the human VR1 gene, which is usually a silent gene or does not produce detectable levels of VR1 receptors, is also available to obtain propriety cells. Such a genetic modification method was described in detail; Nat. Biotechnol., 19, pp 440-445, 2001.

The cells that express human VR1 receptors were maintained in culture flask at 37° C. in an environment containing 5% $CO_2$ until use in the assay. The intracellular $Ca^{2+}$ imaging assay to determine VR1 antagonistic activities was done according to the following procedures.

The culture medium was removed from the flask and fura-2/AM fluorescent calcium indicator was added to the flask at a concentration of 5 µM in the medium. The flask was placed in $CO_2$ incubator and incubated for 1 hour. Then the cells expressing the human VR1 receptors were detached from the flask follow by washing with phosphate buffer saline, PBS(–) and re-suspended in assay buffer. The 80 µl of aliquot of cell suspension ($3.75 \times 10^5$ cells/ml) was added to the assay plate and the cells were spun down by centrifuge (950 rpm, 20° C., 3 minutes).

Capsaicin Stimulation Assay:

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM $MgSO_4$, 1.8 mM $CaCl_2$, 11 mM D-Glucose, 25 mM HEPES, 0.96 mM $Na_2HPO_4$, pH 7.3) was pre-incubated with varying concentrations of the test compounds or KRH buffer (buffer control) for 15 minutes at room temperature under dark conditions. Then the capsaicin solution, which gives 300 nM in assay mixture, was automatically added to the assay plate by the FDSS 6000.

Acid Stimulation Assay:

The Acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) was pre-incubated with varying concentrations of the test compounds or resting buffer (buffer control) for 15 minutes at room temperature under dark conditions. The cells were automatically added the stimulating solution (HBSS supplemented with MES, final assay buffer pH 5.8) by the FDSS 6000. The $IC_{50}$ values of VR1 antagonists were determined from the half of the increase demonstrated by buffer control samples after acidic stimulation.

Determination of Antagonist Activity

The monitoring of the changes in the fluorescence signals ($\lambda ex=340$ nm/380 nm, $\lambda em=510$-520 nm) was initiated at 1 minute prior to the addition of capsaicin solution or acidic buffer and continued for 5 minute. The $IC_{50}$ values of VR1 antagonists were determined from the half of the increase demonstrated by buffer control samples after agonist stimulation.

Chronic Constriction Injury Model (CCI Model):

Male Sprague-Dawley rats (270-300 g; B. W., Charles River, Tsukuba, Japan) were used. The chronic constriction injury (CCI) operation was performed according to the method described by Bennett and Xie (Bennett, G J. and Xie, Y. K. Pain, 33:87-107, 1988). Briefly, animals were anesthetized with sodium pentobarbital (64.8 mg/kg, i.p.) and the left common sciatic nerve was exposed at the level of the middle of the thigh by blunt dissection through the biceps femoris. Proximal to the sciatic's trifurcation was freed of adhering tissue and 4 ligatures (4-0 silk) were tided loosely around it with about 1 mm space. A sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr postdosing. Experimental data were analyzed using Kruskat-Wallis test followed by Dunn's test for multiple comparisons or Mann-Whitney U-test for paired comparison.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.75 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer and incubated for 1 hr. Drug concentration in the buffer was measured by LC/MS analysis. Flux rate (F, mass/time) was calculated from the slope of cumulative appearance of substrate on the receiver side and apparent permeability coefficient ($P_{app}$) was calculated from the following equation.

$$P_{app} (cm/sec)=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity was determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Wallac). All the manipulation, stock solution and equipment was kept on ice at all times. For saturation assays, experiments were conducted in a total volume of 200 μl. Saturation was determined by incubating 20 μl of [$^3$H]-dofetilide and 160 μl of membrane homogenates (20-30 μg protein per well) for 60 min at room temperature in the absence or presence of 10 μM dofetilide at final concentrations (20 μl) for total or nonspecific binding, respectively. All incubations were terminated by rapid vacuum filtration over polyetherimide (PEI) soaked glass fiber filter papers using a Skatron cell harvester followed by two washes with 50 mM Tris buffer (pH 7.5 at 25° C.). Receptor-bound radioactivity was quantified by liquid scintillation counting using a Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM MgCl$_2$, 10 mM KCl so that the final DMSO concentration became equal to 1%. Compounds were dispensed in triplicate in assay plates (4 μl). Total binding and nonspecific binding wells were set up in 6 wells as vehicle and 10 μM dofetilide at final concentration, respectively. The radioligand was prepared at 5.6× final concentration and this solution was added to each well (36 μl). The assay was initiated by addition of YSi poly-L-lysine Scintillation Proximity Assay (SPA) beads (50 μl, 1 mg/well) and membranes (110 μl, 20 μg/well). Incubation was continued for 60 min at room temperature. Plates were incubated for a further 3 hours at room temperature for beads to settle. Receptor-bound radioactivity was quantified by counting with a Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% O$_2$/5% CO$_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; CaCl$_2$, 2; MgCl$_2$, 1; Glucose, 10; HEPES, 5; pH 7.4 with NaOH. Whole-cell recordings were made using a patch clamp amplifier and patch pipettes which have a resistance of 1-3 MOhm when filled with the standard internal solution of the following composition (mM); KCl, 130; MgATP, 5; MgCl$_2$, 1.0; HEPES, 10; EGTA 5, pH 7.2 with KOH. Only those cells with access resistances below 15 MΩ and seal resistances >1 GΩ were accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristaltic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times 100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Drug-Drug Interaction Assay

This method essentially involves determining the percent inhibition of product formation from a fluorescence probe at 3 μM of each compound.

More specifically, the assay is carried out as follows. The compounds were pre-incubated with recombinant CYPs, 100 mM potassium phosphate buffer and fluorescence probe as substrate for 5 min. Reaction was started by adding a warmed NADPH generating system, which consist of 0.5 mM NADP (expect; for 2D6 0.03 mM), 10 mM MgCl$_2$, 6.2 mM DL-Isocitric acid and 0.5 U/ml Isocitric Dehydrogenase (ICD). The assay plate was incubated at 37° C. (expect; for 1A2 and 3A4 at 30° C.) and taking fluorescence readings were taken every minute over 20 to 30 minutes.

Data calculations were performed as follows;
1. The slope (Time vs. Fluorescence units) was calculated at the linear region
2. The percentage of inhibition in compounds was calculated by the equation $$\{(v_o-v_i)/v_o\}\times 100 = \% \text{ inhibition}$$

Wherein
$v_o$=rate of control reaction (no inhibitor)
$v_i$=rate of reaction in the presence of compounds.

TABLE 1

Condition for drug-drug interaction assay.

|  | 1A2 | 2C9 | 2C19 | 2D6 | 3A4 |
|---|---|---|---|---|---|
| Substrate | Vivid blue (Aurora) | MFC (Gentest) | Vivid blue (Aurora) | AMMC (Gentest) | Vivid red (Aurora) |
| Substrate (μM) | 10 | 30 | 10 | 1 | 2 |
| Enzyme (pmol) | 50 | 50 | 5 | 50 | 5 |
| EX./Em(λ) | 408/465 | 408/535 | 408/465 | 400/465 | 530/595 |

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 minute time points, where the 0 minute time point indicated the time when NADPH was added into the reaction mixture of P450 group. An aliquot of samples of non-P450 group was collected at −10 and 65 minute time points. Collected aliquots were extracted with an acetonitrile solution containing an internal standard. The precipitated protein was spun down in a centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln 2/$k$

Mono-Iodoacetate (MIA)-Induced OA Model

Male 6-weeks-old Sprague-Dawley (SD, Japan SLC or Charles River Japan) rats were anesthetized with pentobarbital. Injection site (knee) of MIA was shaved and cleaned with 70% ethanol. Twenty-five μl of MIA solution or saline was injected in the right knee joint using a 29 G needle. The effect of joint damage on the weight distribution through the right (damaged) and left (untreated) knee was assessed using an incapacitance tester (Linton Instrumentation, Norfolk, UK). The force exerted by each hind limb was measured in grams. The weight-bearing (WB) deficit was determined by a difference of weight loaded on each paw. Rats were trained to measure the WB once a week until 20 days post MIA-injection. Analgesic effects of compounds were measured at 21 days after the MIA injection. Before the compound administration, the "pre value" of WB deficit was measured. After the administration of compounds, attenuation of WB deficits was determined as analgesic effects.

Complete Freund's Adjuvant (CFA) Induced Thermal and Mechanical Hyperalgesia in Rats Thermal Hyperalgesia Male 6-week-old SD rats were used. Complete Freund's adjuvant (CFA, 300 μg of *Mycobacterium Tuberculosis* H37RA (Difco, MI) in 100 μL of liquid paraffin (Wako, Osaka, Japan)) was injected into the plantar surface of a hind paw of the rats. Two days after CFA-injection, thermal hyperalgesia was determined by method described previously (Hargreaves et al., 1988) using the plantar test apparatus (Ugo-Basil, Varese, Italy). Rats were adapted to the testing environment for at least 15 minutes prior to any stimulation. Radiant heat was applied to the plantar surface of a hind paw and paw withdrawal latencies (PWL, seconds) were determined. The intensity of radiant heat was adjusted to produce the stable PWL of 10 to 15 seconds. The test compound was administered in a volume of 0.5 mL per 100 g body weight. PWL were measured after 1, 3 or 5 hours after drug administration.

Mechanical Hyperalgesia

Male 4-week-old SD rats were used. CFA (300 μg of *Mycobacterium Tuberculosis* H37RA (Difco, MI) in 100 μL of liquid paraffin (Wako, Osaka, Japan)) was injected into the plantar surface of a hind paw of the rats. Two days after CFA-injection, mechanical hyperalgesia was tested by measuring paw withdrawal threshold (PWT, grams) to pressure using the analgesy-Meter (Ugo-Basil, Varese, Italy). The animals were gently restrained, and steadily increasing pressure was applied to the dorsal surface of a hind paw via a plastic tip. The pressure required to elicit paw withdrawal was determined.

The test compound was administered in a volume of 0.5 mL per 100 g body weight. PWT were measured after 1, 3 or 5 hours after drug administration.

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts.

Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:
(i) where the compound of formula (I) contains a carboxylic acid functionality (—COOH), an ester thereof, for example, replacement of the hydrogen with $(C_1-C_8)$alkyl;
(ii) where the compound of formula (I) contains an alcohol functionality (—OH), an ether thereof, for example, replacement of the hydrogen with $(C_1-C_6)$alkanoyloxymethyl; and
(iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene g!ycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as-silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alernative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as Pleucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10mg of the compound of formula (I). The overall daily dose will typically be in the range 1 µg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;
- a tricyclic antidepressant, e.g. desipramine, imipramine, amitryptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis (trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis (trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
- a vanilloid receptor agonist (e.g. resinferatoxin) or antagonist (e.g. capsazepine);
- a beta-adrenergic such as propranolol;
- a local anaesthetic such as mexiletine;
- a corticosteroid such as dexamethasone;
- a 5-HT receptor agonist or antagonist, particularly a $5\text{-HT}_{1B/1D}$ agonist such as eletriptan, sumatriptan, naratriptan, zolmitriptan or rizatriptan;
- a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol®;
- a PDEV inhibitor, such as 5-[2-ethoxy-5-(4-methyl-1-piperazinyl-sulphonyl)phenyl]-1-methyl-3-n -propyl-1,6-dihydro-7H-pyrazolo[4,3-d]pyrimidin-7-one (sildenafil), (6R,12aR)-2,3,6,7,12,12a -hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl -2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo [4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo [3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy) proline, (2S,4S)-4-(3-fluorobenzyl)-proline, [(1R,5R,6S)-6-(aminomethyl) bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl) amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyidisulfide;

an acetyicholinesterase inhibitor such as donepezil;

a prostaglandin E₂ subtype 4 (EP4) antagonist such as N[({2-[4-(2-ethyl-4,6-dimethyl-1H-imidazo [4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3, 5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The invention is illustrated in the following non-limiting examples in which, unless stated otherwise: all operations were carried out at room or ambient temperature, that is, in the range of from 18° C. to −25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 F₂₅₄ precoated TLC plates), mass spectrometry, nuclear magnetic resonance spectra (NMR), infrared red absorption spectra (IR) or microanalysis. Yields are given for illustrative purposes only. Flash column chromatography was carried out using Merck silica gel 60 (230-400 mesh ASTM) or Biotage amino bounded silica (35-75 μm, KP-NH) or Biotage silica (32-63 μm, KP-Sil). Low-resolution mass spectral data (EI) were obtained on a Integrity (Waters) mass spectrometer. Low-resolution mass spectral data (ESI) were obtained on a ZMD (Micromass) mass spectrometer. NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

EXAMPLE 1

2-(4-TERT-BUTYL-3,5-DIFLUOROPHENOXY)-N-((1R)-1-{3-METHYL-4-[(METHYLSULFONYL)AMINO]PHENYL}ETHYL)ACETAMIDE

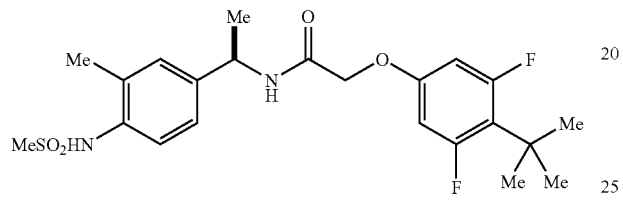

1(a) 4-ACETYL-2-METHYLPHENYL TRIFLUOROMETHANESULFONATE

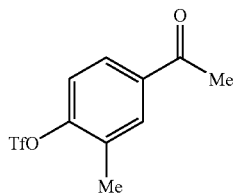

To a stirred solution of 1-(4-hydroxy-3-methylphenyl)ethanone (6.0 g, 40 mmol) in dichloromethane (100 mL) was added triflic anhydride (8.7 mL, 52 mmol) and triethylamine (10 mL) successively. The mixture was stirred at room temperature for 16 hours. It was quenched with water and extracted with dichloromethane. The organic layer was dried over sodium sulfate and concentrated in vacuo. The crude material was purified through silica gel column chromatography eluting with dichloromethane/ethyl acetate (5:1) to furnish 9.6g (85%) of the title compound as a yellow colored oil.

$^1$H NMR (270 MHz, CDCl$_3$) δ 2.45 (3H, s), 2.62 (3H, s), 7.35 (1H, d, J=8.6 Hz), 7.86 (1H, dd, J=8.6, 2.5 Hz), 7.92 (1H, s).

1(b) N(4-ACETYL-2-METHYLPHENYL)METHANESULFONAMIDE

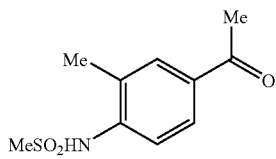

A test tube for use in a microwave was charged with tris(dibenzylidenacetone)dipalladium (0) chloroform adduct (205 mg, 0.20 mmol), 9,9-dimethyl-9H-xanthene-4,5-diyl)bis[diphenylphosphine](345 mg, 0.60 mg, 6.0 mmol), and cesium carbonate(1.63 g, 7.0 mmol). The mixture was subjected to microwave irradiation at 120° C. with stirring for 10 minutes. It was filterd off and the filtrate was concentrated in vacuo. The crude material was purified through silica gel column chromatography eluting with hexane/ethyl acetate (2:1) to furnish 390 mg (34%) of the title compound as a yellow colored solid.

$^1$H NMR (270 MHz, CDCl$_3$) δ 2.34 (3H, s), 2.59 (3H, s), 3.11 (3H, s), 6.47 (1H, br.s), 7.58 (1H, d, J=8.1 Hz), 7.84 (2H, m). MS (ESI) m/z 228 (M+H)$^+$, 226 (M–H)$^-$.

1(c) N-[4-((1R)-1-{[(R)-TERT-BUTYLSULFINYL]AMINO}ETHYL)-2-METHYLPHENYL]METHANESULFONAMIDE

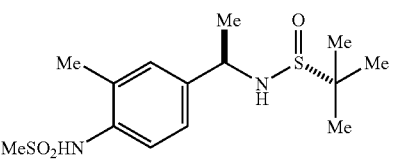

To a solution of titanium(IV) ethoxide (1.32 g, 5.8 mol) and N-(4-acetyl-2-methylphenyl) methanesulfonamide (800 mg, 3.5 mmol) in tetrahydrofuran (20 mL) was added (R)-(+)-2-methyl-2-propanesulfinamide (423 mg, 350 mmol) under a nitrogen atmosphere and the mixture was heated at 70° C. for 16 hours. It was quenched with water and the resulting white precipitate was filtered off. The filtrate was partitioned between ethyl acetate and water. The organic layer was dried over sodium sulfate and concentrated in vacuo. The crude material was purified by silica gel column chromatography, eluting with hexane/ethyl acetate (4:1). The yellow oil obtained was dissolved in tetrahydrofuran (10 mL) and the solution was added to sodium borohydride (242 mg, 6.4 mmol) in tetrahydrofuran (10 mL) at –70° C. The mixture was stirred at –70° C. for 5 hours and then quenched with methanol. It was stirred at room temperature for 1 hour and concentrated in vacuo to furnish 530 mg (45%) of the title compound. MS (ESI) m/z 333 (M+H)$^+$, 331 (M–H)$^-$.

1(d) N-{4-[(1R)-1-AMINOETHYL]-2-METHYLPHENYL}METHANESULFONAMIDE HYDROCHLORIDE

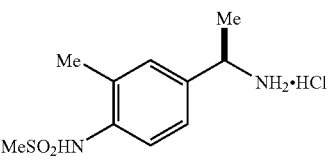

To N-[4-((1R)-1-{[(R)-tert-butylsulfinyl]amino}ethyl)-2-methylphenyl]methanesulfonamide (530 mg, 1.60 mmol) was added HCl-methanol (2.0 M, 5.0 mL) and 1,4-dioxane (5.0 mL). The solution was stirred at room temperature for 30 minutes and then concentrated in vacuo. Diethyl ether was added to precipitate amine hydrochloride. The precipitate was then filtered and washed with diethyl ether (450 mg, quant) to furnish the title compound as a white solid.

$^1$H NMR (270 MHz, DMSO-d6) δ 1.45 (3H, m), 2.31 (3H, s), 2.98 (3H, s), 4.27 (1H, m), 7.31-7.38 (2H, m). MS (ESI) m/z 227 (M−H)$^−$.

1(e) 2-(4-TERT-BUTYL-3,5-DIFLUOROPHE-NOXY)-N-((1R)-1-{3-METHYL-4-[(METHYL-SULFONYL)AMINO]PHENYL}ETHYL)ACETA-MIDE

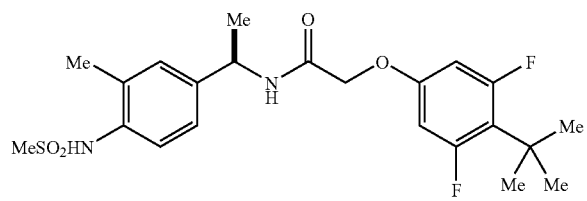

To a tetrahydrofuran (THF) (3.0 ml) solution of (4-tert-butyl-3,5-difluorophenoxy)acetic acid (166 mg, 0.68 mmol) was added 2-chloro-1,3-dimethylimidazolinium chloride (CDI) (110 mg, 0.68 mmol) at room temperature and the mixture was stirred for 2 hours, followed by the addition of triethylamine (0.5 ml) and N-{4-[(1R)-1-aminoethyl]-2-methylphenyl}methanesulfonamide hydrochloride (180 mg, 0.68 mmol) with stirring for 10 hours. The reaction was partitioned with water and dichloromethane and the organic layer was separated and dried over sodium sulfate. Then filtration and evaporation under reduced pressure gave the crude residue which was purified by silica gel column chromatography, eluting with dichloromethane/methanol from 5:1 to 5:2, to furnish 1 16mg (38%) of the title compound as a white solid.

$^1$H-NMR (270 MHz, CDCl$_3$) δ 1.43 (9H, s), 1.53 (3H, d, J=6.6 Hz), 2.31 (3H, s), 3.02 (3H, s), 4.44 (2H, d, J=3.3 Hz), 5.16 (1H, m), 6.25 (1H, br.s), 6.41 (2H, d, J=12 Hz), 6.64 (1H, d, J=7.9 Hz), 7.16 (2H, m), 7.42 (1H, d, J=8.6 Hz). MS (ESI) m/z 445 (M+H)$^+$, 443 (M−H)$^−$

EXAMPLE 2

2-(4-TERT-BUTYL-3,5-DIFLUOROPHENOXY)-N-((1R)-1-{3-FLUORO-4-[(METHYLSULFONYL)AMINO]PHENYL}ETHYL)ACETAMIDE

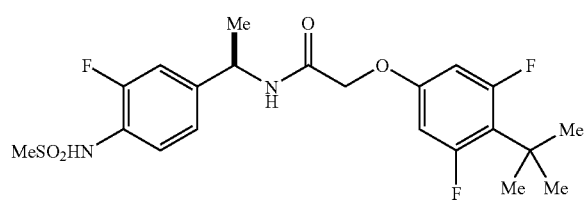

(4-tert-Butyl-3,5-difluorophenoxy)acetic acid (166 mg, 0.68 mmol), 2-chloro-1,3-dimethylimidazolinium chloride (CDI) (110 mg, 0.68 mmol), triethylamine (0.5 ml) and N-{4-[(1R)-1-aminoethyl]-2-fluorophenyl}methanesulfonamide hydrochloride (183 mg, 0.68 mmol) were mixed by the same procedure as described in Example 1(e) to give 115 mg (37%) of the title compound as a white solid.

$^1$H-NMR (270 MHz, CDCl$_3$) δ 1.43 (9H, s), 1.53 (3H, d, J=6.6 Hz), 3.02 (3H, s), 4.45 (2H, d, J=2.9 Hz), 5.17 (1H, m), 6.41 (2H, d, J=12 Hz), 6.68 (2H, m), 7.09 (2H, t, J=8.1 Hz), 7.53 (1H, t, J=8.1 Hz). MS (ESI) m/z 459 (M+H)$^+$, 457 (M−H)$^−$

EXAMPLE 3

2-(4-TERT-BUTYL-3,5-DIFLUOROPHENOXY)-N-((1R)-1-{4-[(METHYLSULFONYL)AMINO]PHENYL}ETHYL)ACETAMIDE

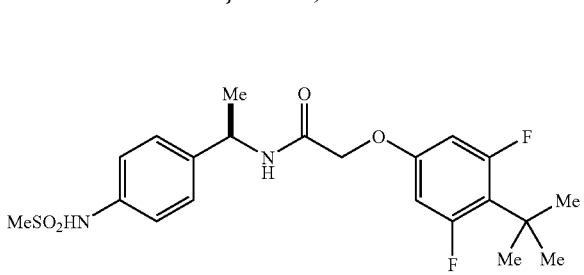

((4-tert-Butyl-3,5-difluorophenoxy)acetic acid (147 mg, 0.60 mmol), 2-chloro-1,3-dimethylimidazolinium chloride (CDI) (102 mg, 0.63 mmol), triethylamine (0.5 ml) and N-{4-[(1R)-1-aminoethyl]phenyl}methanesulfonamide hydrochloride (150 mg, 0.60 mmol) were mixed by the same procedure as described in Example 1(e) to give 167 mg (63%) of the title compound as a white solid.

$^1$H-NMR (270 MHz, CDCl$_3$) δ 1.43 (9H, s), 1.54 (3H, d, J=7.3 Hz), 3.01 (3H, s), 4.44 (2H, d, J=2.6 Hz), 5.19 (1H, m), 6.40 (2H, d, J=12 Hz), 6.65 (1H, m), 7.19 (2H, J=8.6 Hz), 7.31 (2H, d, J=8.6 Hz). MS (ESI) m/z 441 (M+H)$^+$, 439 (M−H)$^−$

EXAMPLE 4

2-(4-TERT-BUTYL-3,5-DIFLUOROPHENOXY)-N-((1R)-1-{3-(HYDROXYMETHYL)-4-[(METHYLSULFONYL)AMINO]PHENYL}ETHYL)ACETOAMIDE

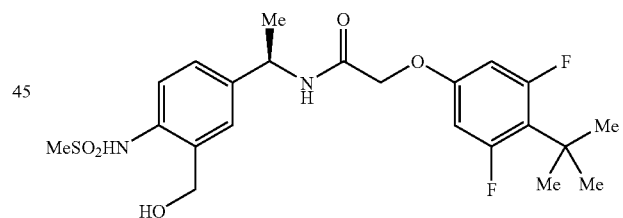

4(a) ETHYL 5-((1R)-1-{[(R)-TERT-BUTYLSULFINYL]AMINO}ETHYL)-2-[(METHYLSULFONYL)AMINO]BENZOATE

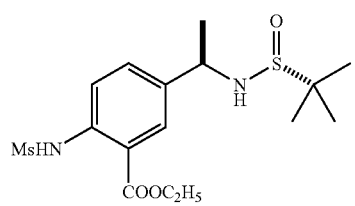

To a mixture of methyl 5-acetyl-2-[(methylsulfonyl) amino]benzoate (13.2 g, 49 mmol, PCT Int. Appl. WO2005003084) in titanium (IV) ethoxide (100 ml) and tetrahydrofuran (THF) (100 ml) was added (R)-(+)-2-methylpropane-2-sulfinamide (5.9 g, 49 mmol, Advanced Asymmmetry) and the mixture was stirred for 16 hours at 80° C. The mixture was cooled to room temperature and then to 0° C. before it was added dropwise into a 0° C. solution of sodium borohydride (7.4 g, 195 mmol). Thre mixture was stirred at 0° C. for 3 hours and then warmed to room temperature. The reaction was quenched with methanol and stirred for 30 minutes. Water was added to the mixture and it was stirred for 10 minutes. The resulting suspension was filtered through a pad of Celite and the filter cake was washed with ethyl acetate. The filtrate was concentrated under reduced pressure to give the residue, which was applied to a silica gel chromatography column and eluted with a volume mixture of dichloromethane and ethyl acetate (1:1) to furnish 4.3 g (23% yield) of the title compound as a slightly yellow solid.

$^1$H-NMR (270 MHz, CDCl$_3$) δ ppm 1.24 (9H, s), 1.43 (3H, t, J=6.8 Hz), 1.53 (3H, d, J=6.6 Hz), 3.07 (3H, s), 3.39 (1H, br.s), 4.41 (2H, q, J=6.8 Hz), 4.55 (1H, m), 7.56 (1H, dd, J=8.6, 2.0 Hz), 7.74 (1H, d, J=9.2 Hz), 8.06 (1H, d, J=2.0 Hz), 10.49 (1H, br.s). MS (ESI) m/z 391 [M+H]$^+$, 389 [M–H]$^-$.

4(b) ETHYL 5-[(1R)-1-AMINOETHYL]-2-[(METHYLSULFONYL)AMINO]BENZOATE

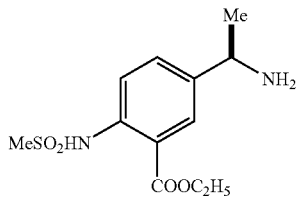

To a solution of ethyl 5-((1R)-1-{[(R)-tert-butylsulfinyl] amino}ethyl)-2-[(methylsulfonyl)amino]benzoate (4.3 g,11 mmol) in methanol (30 ml) was added hydrogenchloride-methanol solution (30 ml). The solution was stirred at room temperature for 30 minutes and then concentrated under reduced pressure. The given residue was recrystallized from methanol-diethyl ether. The precipitate was then filtered, washed with diethyl ether and collected to furnish 3.1 g (87% yield) of the title compound as a white solid.

$^1$H NMR (270 MHz, DMSO-d6) δ ppm 1.34 (3H, t, J=7.3 Hz), 1.49 (3H, d, J=7.3 Hz), 3.19 (3H, s), 4.36 (2H, q, J=7.3 Hz), 4.45 (1H, m), 7.61 (1H, d, J=8.6 Hz), 7.75 (1H, dd, J=8.6, 2.0 Hz), 8.09 (1H, d, J=2.0 Hz), 8.35 (2H, br.s), 10.14 (1H, br.s).

4(c) N-[4-((1R)-1-{[(R)-TERT-BUTYLSULFINYL]AMINO}ETHYL)-2-(HYDROXYMETHYL)PHENYL]METHANESULFONAMIDE

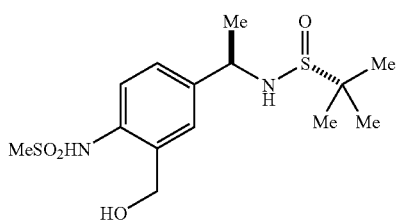

To a mixture of lithium alminium hydride (1.6 g, 43 mmol) in tetrahydrofuran (THF) (50 ml) was added a solution of ethyl 5-((1R)-1-{[(R)-tert-butylsulfinyl]amino}ethyl)-2-[(methylsulfonyl)amino]benzoate (4.2 g, 11 mmol) in tetrahydrofuran (THF) (100 ml) at 0° C. After being stirred for 3 hours at 0° C., potassium fluoride and sodium sulfate decahydrate were added. After being stirred for 5 hours, the reaction mixture was filtered and the filtrate was evaporated under reduced pressure to give 3.6 (97% yield) of the title compound as slightly yellow oil. MS (ESI) m/z 391 [M+H]$^+$, 389 [M–H]$^-$.

4(d) N-[4-[(1R)-1-AMINOETHYL]-2-(HYDROXYMETHYL)PHENYL]METHANESULFONAMIDE HYDROCHLORIDE

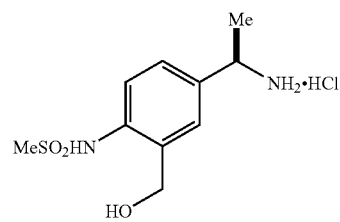

To a solution of N-[4-((1R)-1-{[(R)-tert-butylsulfinyl] amino}ethyl)-2-(hydroxymethyl)phenyl]methanesulfonamide (3.6 g,10 mmol) in methanol (30 ml) was added hydrogenchloride-methanol solution (30 ml). The solution was stirred at room temperature for 30 minutes and then concentrated under reduced pressure. The given residue was recrystallized from methanol-diethyl ether. The precipitate was then filtered, washed with diethyl ether and collected to furnish 2.5 g (87% yield) of the title compound as a yellow oil.

$^1$H NMR (270 MHz, DMSO-d6) δ ppm 1.51 (3H, t, J=6.6 Hz), 3.01 (3H, s), 4.36 (1H, m), 4.63 (2H, s), 7.34 (1H, d, J=7.9 Hz), 7.45 (1H, dd, J=7.9, 2.0 Hz), 7.58 (1H, d, J=2.0 Hz), 8.56 (2H, br.s), 9.13 (1H, br.s). MS (ESI) m/z 243 [M–H]$^-$.

4(e) 2-(4-TERT-BUTYL-3,5-DIFLUOROPHENOXY)-N-((1R)-1-{3-(HYDROXYMETHYL)-4-[(METHYLSULFONYL)AMINO]PHENYL}ETHYL)ACETAMIDE

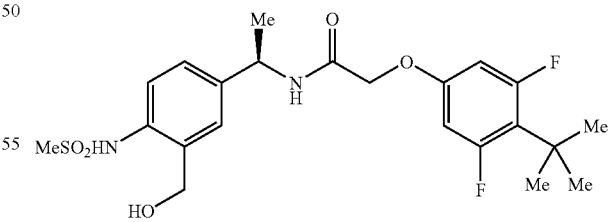

To a solution of N-[4-[(1R)-1-aminoethyl]-2-(hydroxymethyl)phenyl]methanesulfonamide hydrochloride (40 mg, 0.14 mmol) in N,N-dimethylformamide (DMF) (2 ml), (4-tert-butyl-3,5-difluorophenoxy)acetic acid (34 mg, 0.14 mmol), N-(3-dimethylaminopropyl)-N'-ethylcarbodiimide (40 mg), and 4-dimethylaminopyridine (DMAP) (0.5 mg, 0.004 mmol) were added. The solution was stirred at room temperature for 16 hours and then partitioned between ethyl acetate and water. The organic layer was dried over sodium sulfate, filtered, and evaporated. The residue obtained was purified by silica gel column chromatography, eluting with methylene chloride/ethylacetate (1:1), to give 2-(4-tert-butyl-3,5-difluorophenoxy)-N-((1R)-1-{3-(hydroxymethyl)-4-[(methylsulfonyl)amino]phenyl}ethyl)acetamide (24 mg, 36%).

$^1$H NMR (270 MHz, DMSO-d6) δ ppm 1.43 (9H, s), 1.52 (3H, d, J=7.3 Hz), 2.75 (1H, br.s), 3.03 (3H, s), 4.40 (2H, d, J=4.0 Hz), 4.71 (2H, br.s), 5.14 (1H, m), 6.40 (2H, d, J=12 Hz), 6.68 (1H, d, J=7.9 Hz), 7.17 (1H, d, J=2.6 Hz), 7.24 (1H, d, J=2.6 Hz), 7.50 (1H, d, J=8.6 Hz), 7.84 (1H, br.s). MS (ESI) m/z 469 [M −H]$^-$.

EXAMPLE 5

2-[3,5-DIFLUORO-4-(2,2,2-TRIFLUORO-1,1-DIMETHYLETHYL)PHENOXY]-N-((1R)-1-{3-METHYL-4-[(METHYLSULFONYL)AMINO]PHENYL}ETHYL)ACETAMIDE

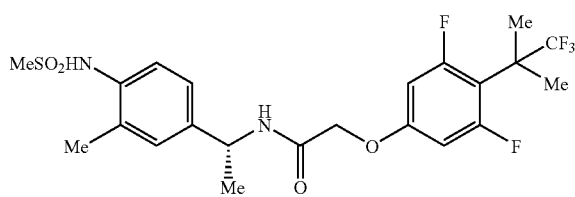

5a) 2-(2,6-DIFLUORO-4-METHOXYPHENYL)-1,1,1-TRIFLUOROPROPANE-2-ol

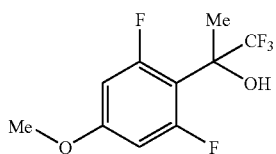

To a tetrahydrofuran (100 ml) solution of 1,3-difluoro-5-methoxybenzene (7 g, 48.6 mmol) was added 1.6 M hexane solution of n-butyllithium (30 ml, 48.6 mmol) dropwise at −78° C. over 30 minutes and the mixture was stirred for 2 hours at −78° C. 1,1,1-Trifluoroacetone (6.5 g, 58.3 mmol) was added at −78° C. and the mixture was stirred for 2 hours at −78° C. followed by additional stirring for 1 hour at room temperature. Then, the reaction was diluted with water and the product was extracted with ethyl acetate. Then, the organic layer was filtrated, evaporated and concentrated. The residue was purified by silica gel column chromatography, eluting with hexane/ethyl acetate (10:1), to furnish 9.7 g (78% yield) of the title compound as a colorless oil.

$^1$H NMR (CDCl$_3$, 270 MHz) δ ppm 1.83-1.85 (3H, m), 3.94 (3H, s), 6.17 (1H, s), 6.49-6.60 (2H, m)

5b) 2-(1-CHLORO-2,2,2-TRIFLUORO-1-METHYLETHYL)-1,3-DIFLUORO-5-METHOXYBENZENE

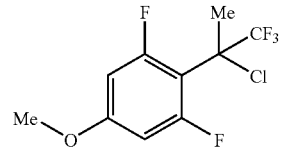

A thionyl chloride (25 ml) solution of 2-(2,6-difluoro-4-methoxyphenyl)-1,1,1-trifluoropropan-2-ol (8.7 g, 34.1 mmol) and pyridine (26 mg, 0.34 mmol) was stirred at 70° C. for 3 hours. Then, the reaction was concentrated in vacuo and diluted with water. The product was extracted with hexane and the organic layer was dried over sodium sulfate, filtered and concentrated to furnish 8.84 g (94% yield) of the title compound as a colorless oil.

$^1$H NMR (CDCl$_3$, 270 MHz) δ ppm 2.24-2.29 (3H, m), 3.81 (3H, s), 6.44-6.54 (2H, m)

5c) 1,3-DIFLUORO-5-METHOXY-2-(2,2,2-TRIFLUORO-1,1-DIMETHYLETHYL)BENZENE

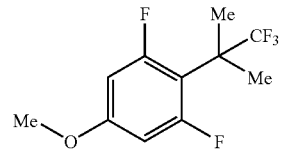

To a cyclohexane (100 ml) solution of 2-(1-chloro-2,2,2-trifluoro-1-methylethyl)-1,3-difluoro-5-methoxybenzene (8.84 9, 32.2 mmol) was added 1.0 M hexane solution of trimethylaluminum (129 ml, 129 mmol) at room temperature and the mixture was stirred under reflux condition for 4 hours. Then, the reaction was quenched with 2 N-hydrochloride aqueous solution and the product was extracted with hexane which was dried over sodium sulfate, filtration and evaporation to furnish 7.9 g (97% yield) of the title compound as a colorless oil.

$^1$H NMR (CDCl$_3$, 300 MHz) δ ppm 1.71 (6H, s), 3.78 (3H, s), 6.39-6.49 (2H, m)

5d) 3,5-DIFLUORO-4-(2,2,2-TRIFLUORO-1,1-DIMETHYLETHYL)PHENOL

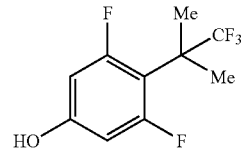

A mixture of 1,3-difluoro-5-methoxy-2-(2,2,2-trifluoro-1,1-dimethylethyl)benzene (7.93 g, 31.2 mmol) and 1 M dichloromethane solution of boron tribromide (150 ml, 150 mmol) was stirred at room temperature for 16 hours. Then, the reaction was quenched with water and the product was extracted with ethyl acetate which was dried over sodium sulfate. Then, filtration, evaporation, purification by silica gel column chromatography, eluting with hexane/ethy lacetate (10:1), furnished 7.79 g (quant.) of the title compound as a brown solid.

$^1$H NMR (CDCl$_3$, 270 MHz) δ ppm 1.71 (6H, s), 5.27 (1H, brs), 6.36-6.50 (2H, m)

5e) ETHYL[3,5-DIFLUORO-4-(2,2,2-TRIFLUORO-1,1-DIMETHYLETHYL)PHENOXY]ACETATE

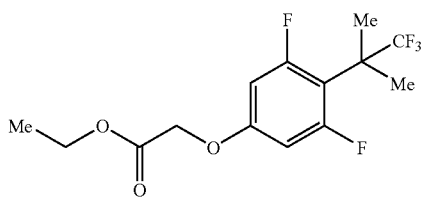

An acetone (5 ml) suspension of 3,5-difluoro-4-(2,2,2-trifluoro-1,1-dimethylethyl)phenol (227 mg, 0.95 mmol), ethyl bromoacetate (174 mg, 1.0 mmol) and potassium carbonate (261 mg, 1.9 mmol) was stirred at reflux for 1 hour. Then, the reaction was quenched with water and the product was extracted with ethyl acetate. The organic layer was dried over sodium sulfate, filtrated and evaporated to furnish 267 mg (87% yield) of the title compound as colorless oil.

$^1$H NMR (CDCl$_3$, 270 MHz) δ ppm 1.31 (3H, t, J=6.9 Hz), 1.70-1.73 (6H, m), 4.29 (2H, q, J=6.9 Hz), 4.58 (2H, s), 6.39-6.49 (2H, m)

5f) [3,5-DIFLUORO-4-(2,2,2-TRIFLUORO-1,1-DIMETHYLETHYL)PHENOXY]ACETIC ACID

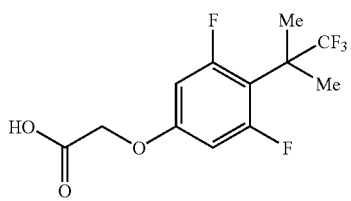

To a tetrahydrofuran (1 ml) solution of ethyl [3,5-difluoro-4-(2,2,2-trifluoro-1,1-dimethylethyl)phenoxy]acetate (267 mg, 0.82 mmol) and methanol (1.5 ml) was added 2 N sodium hydroxide aqueous solution (1 ml) and the mixture was stirred at 60° C. for 30 minutes. After the reaction was complete, the basic mixture was acidified with 2 N hydrochloride aqueous solution and the product was extracted with ethyl acetate which was dried over sodium sulfate. The organic layer was filtered and concentrated to give 242 mg (99% yield) of the title compound as a brown solid.

$^1$H NMR (CDCl$_3$, 270 MHz) δ ppm 1.69-1.72 (6H, m), 4.66 (2H, s), 6.42-6.50 (2H, m) MS (ESI) m/z 297 (M−H)$^−$.

5g) 2-[3,5-DIFLUORO-4-(2,2,2-TRIFLUORO-1,1-DIMETHYLETHYL)PHENOXY]-N-((1R)-1-{3-METHYL- 4-[(METHUYLSULFONYL)AMINO]PHENYL}ETHYL)ACETAMIDE

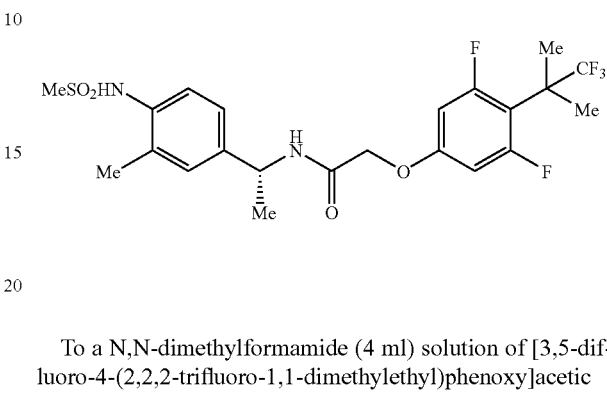

To a N,N-dimethylformamide (4 ml) solution of [3,5-difluoro-4-(2,2,2-trifluoro-1,1-dimethylethyl)phenoxy]acetic acid (120 mg, 0.40 mmol), N{4-[(1R)-1-aminoethyl]-2-methylphenyl}methanesulfonamide hydrochloride (116 mg, 0.44 mmol) and triethylamine (121 mg, 1.2 mmol) was added 2-(1H-benzotriazol-1-yl)-1,1,3,3-tetramethyluronium hexafluorophosphate (HBTU) (182 mg, 0.48 mmol) and the mixture was stirred for 1 hour at room temperature. Then, the reaction was quenched with saturated sodium bicarbonate aqueous solution and the product was extracted with ethyl acetate/hexane (3:1), which was dried over sodium sulfate. Then, the organic layer was filtered, and concentrated. The residue was purified by silica gel column chromatography eluting with hexane/ethyl acetate (1:1) and preparative HPLC eluting with acetonitrile/0.05% formic acid aqueous solution (32:68 to 68:32) to furnish 102 mg (50% yield) of the title compound as a white solid.

$^1$H NMR (CDCl$_3$, 300M Hz) δ ppm 1.52 (3H, d, J=7.3 Hz), 1.70-1.74 (6H, m), 2.31 (3H, s), 3.03 (3H, s), 4.40-4.52 (2H, m), 5.14-5.22 (1H, m), 6.16 (1H, brs), 6.42-6.53 (2H, m), 6.58-6.60 (1H, m), 7.15-7.25 (2H, m), 7.42 (1H, d, J=8.8 Hz) MS (ESI): m/z 509 (M+H)$^+$, 507 (M−H)$^−$.

All the Examples described above were tested in the human VR1 antagonist assay and the HLM half-life test method described hereinabove.

TABLE 1

Results of Human VR1 antagonist assay and half-life in HLM

| Example | hVR1 IC$_{50}$ (nM) | Half-life in HLM (min) |
|---------|---------------------|------------------------|
| 1       | 3.13                | 31                     |
| 2       | 31.29               | 12                     |
| 3       | 34.39               | 48                     |
| 4       | 8.70                | 5.8                    |
| 5       | 7.55                | 13                     |

IC$_{50}$: the concentration of the individual compound required to reduce Ca$^{2+}$ influx capsaicin-evoked by 50%.

The invention claimed is:

1. A compound of the formula (I):

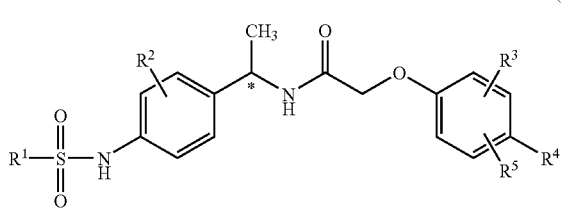

wherein $R^1$ represents $(C_1-C_6)$alkyl;

$R^2$ represents hydrogen, halogen, hydroxy, $(C_1-C_6)$alkyl, $(C_1-C_6)$alkoxy, hydroxy$(C_1-C_6)$ alkyl, $(C_1-C_6)$alkoxy-$(C_1-C_6)$alkyl or halo$(C_1-C_6)$alkyl;

$R^3$ represents a halogen atom, $(C_1-C_6)$alkyl, $(C_1-C_6)$ alkoxy, hydroxy$(C_1-C_6)$alkoxy, $(C_1-C_6)$ alkoxy-$(C_1-C_6)$ alkyl, $(C_1-C_6)$alkoxy-$(C_1-C_6)$alkoxy, halo$(C_1-C_6)$alkyl, $(C_1-C_6)$ alkylthio, $(C_1-C_6)$ alkylsulfinyl, $(C_1-C_6)$alkylsulfonyl, $[(C_1-C_6)$alkyl$]$NH—, or$[(C_1-C_6)$alkyl$]_2$N—;

$R^4$ represents a halogen atom, $(C_1-C_6)$alkyl, halo$(C_1-C_6)$ alkyl, $(C_1-C_6)$alkoxy, hydroxy$(C_1-C_6)$ alkoxy, $(C_1-C_6)$ alkoxy-$(C_1-C_6)$alkyl, $(C_1-C_6)$alkoxy-$(C_1-C_6)$alkoxy, $[(C_1-C_6)$ alkyl$]$NH—, or$[(C_1-C_6)$alkyl$]_2$N—;

$R^5$ represents a halogen atom, $(C_1-C_6)$alkyl, $(C_1-C_6)$ alkoxy, hydroxy$(C_1-C_6)$alkoxy, $(C_1-C_6)$ alkoxy-$(C_1-C_6)$ alkyl, $(C_1-C_6)$alkoxy-$(C_1-C_6)$alkoxy, halo$(C_1-C_6)$alkyl, $(C_1-C_6)$alkylthio, $(C_1-C_6)$alkylsulfinyl, $(C_1-C_6)$alkylsulfonyl, $[(C_1-C_6)$alkyl$]$NH—, $[(C_1-C_6)$alkyl$]_2$N—, $H_2N$—$(C_1-C_6)$alkoxy, $(C_1-C_6)$alkyl-NH—$(C_1-C_6)$alkoxy, $[(C_1-C_6)$alkyl$]_2$N—$(C_1-C_6)$alkoxy, $H_2N$—$(C_1-C_6)$alkoxy-$(C_1-C_6)$alkyl, $(C_1-C_6)$alkyl-NH—$(C_1-C_6)$alkoxy-$(C_1-C_6)$alkyl, or $[(C_1-C_6)$alkyl$]_2N(C_1-C_6)$alkoxy-$(C_1-C_6)$alkyl; and

* indicates a chiral centre;

or a pharmaceutically acceptable salt or solvate thereof.

2. A compound according to claim 1, wherein $R^1$ represents methyl.

3. A compound according to claim 1, wherein $R^2$ represents hydrogen, hydroxy, hydroxymethyl, fluoro, chloro or methoxy.

4. A compound according to claim 1, wherein $R^3$ represents halogen or $(C_1-C_3)$alkoxy.

5. A compound according to claim 1, wherein $R^3$ represents fluoro.

6. A compound according to claim 1, wherein $R^4$ represents $(C_1-C_6)$alkyl, or halo$(C1-C_6)$alkyl.

7. A compound according to claim 1, wherein $R^4$ represents tert-butyl or 2,2,2-trifluoro-1,1-dimethylethyl.

8. A compound according to claim 1, wherein $R^5$ represents halogen or $(C_1-C_3)$alkoxy.

9. A compound according to claim 1, wherein $R^5$ represents fluoro.

10. A compound according to claim 1 to selected from the group consisting of:
- 2-(4-tert-butyl-3,5-difluorophenoxy)-N-(1-{3-methyl-4-[(methylsulfonyl) amino]phenyl}ethyl)acetamide;
- 2-(4-tert-butyl-3,5-difluorophenoxy)-N-(1-{3-fluoro-4-[(methylsulfonyl) amino]phenyl}ethyl)acetamide;
- 2-(4-tert-butyl-3,5-difluorophenoxy)-N-(1-{4-[(methylsulfonyl) amino]phenyl}ethyl)acetamide;
- 2-(4-tert-butyl-3,5-difluorophenoxy)-N-(1-{3-hydroxymethyl-4-[(methylsulfonyl) amino]phenyl}ethyl)acetamide; and
- 2-(4-{2,2,2-trifluoro-1;1-dimethylethyl)-3,5-difluorophenoxy)-N-(1-{3-methyl-4-[(methylsulfonyl) amino] phenyl}ethyl)acetamide;

or a pharmaceutically acceptable salt or solvate thereof.

11. A compound according to claim 1, wherein the compounds of formula (I) have (R) stereochemistry at the position marked *.

12. A pharmaceutical composition comprising a compound of the formula (I), or a pharmaceutically acceptable salt or solvate thereof, as defined in claim 1, together with a pharmaceutically acceptable excipient.

* * * * *